(12) United States Patent
Harper et al.

(10) Patent No.: US 11,653,967 B2
(45) Date of Patent: May 23, 2023

(54) SYSTEM AND METHOD FOR BALLOON DIAMETER HYSTERESIS COMPENSATION

(71) Applicant: Boston Scientific Scimed, Inc., Maple Grove, MN (US)

(72) Inventors: Keegan Harper, Encinitas, CA (US); Chadi Harmouche, Saint-Laurent (CA); Eugene J. Jung, San Diego, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 388 days.

(21) Appl. No.: 16/402,802

(22) Filed: May 3, 2019

(65) Prior Publication Data

US 2019/0336193 A1 Nov. 7, 2019

Related U.S. Application Data

(60) Provisional application No. 62/666,230, filed on May 3, 2018.

(51) Int. Cl.
| | |
|---|---|
| *A61B 18/02* | (2006.01) |
| *A61B 18/00* | (2006.01) |
| *A61M 25/10* | (2013.01) |

(52) U.S. Cl.
CPC ...... *A61B 18/02* (2013.01); *A61B 2018/0022* (2013.01); *A61B 2018/0066* (2013.01); *A61B 2018/00351* (2013.01); *A61B 2018/00577* (2013.01); *A61B 2018/00744* (2013.01); *A61B 2018/00922* (2013.01); *A61B 2018/0212* (2013.01); *A61B 2018/0262* (2013.01); *A61M 25/10184* (2013.11)

(58) Field of Classification Search
CPC ............... A61B 18/02; A61B 18/0022; A61B 2018/0212; A61B 2018/0262; A61M 25/10184; A61M 2025/1068
See application file for complete search history.

(56) References Cited

U.S. PATENT DOCUMENTS

| | | |
|---|---|---|
| RE32,983 E | 7/1989 | Levy |
| 4,906,244 A | 3/1990 | Pinchuk |
| 5,017,325 A | 5/1991 | Jackowski et al. |

(Continued)

FOREIGN PATENT DOCUMENTS

| | | |
|---|---|---|
| CA | 2816573 | 6/2012 |
| CN | 103930061 B | 9/2016 |

(Continued)

*Primary Examiner* — Daniel W Fowler
(74) *Attorney, Agent, or Firm* — Nelson Mullins Riley & Scarborough LLP

(57) ABSTRACT

A balloon catheter system for use by an operator for treating a targeted vein, the balloon catheter system comprising a balloon catheter, a fluid source and a control system. The balloon catheter includes a balloon having a balloon interior, the balloon configured to undergo one or more inflation cycles. The fluid source contains a cryogenic fluid that is selectively delivered to the balloon interior. The control system is configured to selectively control the delivery of the fluid to the balloon interior and to that selectively adjusts an inflation pressure to of the balloon interior based on a number of inflation cycles undergone by the balloon so as to selectively adjust an inflated balloon diameter of the balloon.

19 Claims, 8 Drawing Sheets

(56) References Cited

U.S. PATENT DOCUMENTS

| | | |
|---|---|---|
| 5,024,668 A | 6/1991 | Peters et al. |
| 5,108,415 A | 4/1992 | Pinchuk et al. |
| 5,470,313 A | 11/1995 | Crocker et al. |
| 5,500,180 A * | 3/1996 | Anderson ............... A61L 2/206 |
| | | 264/532 |
| 5,569,195 A | 10/1996 | Saab |
| 5,868,705 A * | 2/1999 | Bagaoisan .............. A61L 29/00 |
| | | 604/103.11 |
| 5,951,941 A | 9/1999 | Wang et al. |
| 6,146,356 A | 11/2000 | Wang et al. |
| 6,547,788 B1 | 4/2003 | Maguire et al. |
| 6,572,813 B1 | 6/2003 | Zhang et al. |
| 6,575,933 B1 | 6/2003 | Wittenberger et al. |
| 6,645,422 B2 | 11/2003 | Jung, Jr. et al. |
| 6,666,858 B2 | 12/2003 | Lafontaine |
| 6,685,732 B2 | 2/2004 | Kramer |
| 6,709,431 B2 | 3/2004 | Lafontaine |
| 6,989,009 B2 | 1/2006 | Lafontaine |
| 7,189,227 B2 | 3/2007 | Lafontaine |
| 7,879,270 B2 | 2/2011 | Varma et al. |
| 9,033,965 B2 | 5/2015 | Ingle et al. |
| 9,526,814 B2 | 12/2016 | Weber et al. |
| 9,545,216 B2 | 1/2017 | D'Angelo et al. |
| 9,757,050 B2 | 9/2017 | Ghaffar et al. |
| 2005/0165388 A1 * | 7/2005 | Bhola ................ A61B 18/1492 |
| | | 606/14 |
| 2008/0255512 A1 * | 10/2008 | Krivoruchko ..... A61M 25/1027 |
| | | 604/103.09 |
| 2010/0241113 A1 * | 9/2010 | Ingle ..................... A61B 18/02 |
| | | 606/21 |
| 2012/0271339 A1 * | 10/2012 | O'Beirne ............ A61M 25/104 |
| | | 606/194 |
| 2015/0367106 A1 | 12/2015 | Nitsan et al. |
| 2016/0008589 A1 | 1/2016 | Stupecky et al. |
| 2017/0265924 A1 | 9/2017 | Kochavi |
| 2018/0085499 A1 | 3/2018 | Wang et al. |

FOREIGN PATENT DOCUMENTS

| | | |
|---|---|---|
| CN | 103147188 B | 2/2017 |
| JP | 2005-503241 A | 2/2005 |
| JP | 2006-524116 A | 10/2006 |

\* cited by examiner

| Balloon Catheter Compliance | | | | |
|---|---|---|---|---|
| Pressure (psig) | Cath 161 O.D (mm) | Cath 162 O.D (mm) | Cath 163 O.D (mm) | Average O.D (mm) |
| 2.5 | 28.5 | 28.9 | 28 | 28.5 |
| 3 | 29.2 | 29.3 | 28.7 | 29.1 |
| 4 | 29.9 | 30 | 29.6 | 29.8 |
| 5 | 30.2 | 30.3 | 30.2 | 30.2 |
| 6 | 30.4 | 30.5 | 30.5 | 30.5 |
| 7 | 30.9 | 30.7 | 30.7 | 30.8 |
| 8 | 31.2 | 30.9 | 31.1 | 31.1 |
| 9 | 31.4 | 31.4 | 31.3 | 31.4 |
| 10 | 31.6 | 31.6 | 31.6 | 31.6 |
| 11 | 32 | 31.9 | 31.9 | 31.9 |
| 12 | | 32.1 | 32.2 | 32.2 |

| Hysteresis Measurements | | | | | |
|---|---|---|---|---|---|
| Pressure (psig) | Cath 161 O.D (mm) | Cath 162 O.D (mm) | Cath 163 O.D (mm) | Average (mm) | Std. Dev (mm) |
| 2.5 | 29.5 | 29.4 | 28.7 | 29.2 | 0.36 |
| 3.0 | 29.8 | 29.8 | 29.0 | 29.5 | 0.38 |
| 4.0 | 30.2 | 30.3 | 29.6 | 30.0 | 0.31 |
| 5.0 | 30.4 | 30.5 | 30.2 | 30.4 | 0.12 |
| 6.0 | 30.7 | 30.7 | 30.6 | 30.7 | 0.05 |
| 7.0 | 30.9 | 31.0 | 30.7 | 30.9 | 0.12 |
| 8.0 | 31.2 | 31.2 | 30.9 | 31.1 | 0.14 |
| 9.0 | 31.4 | 31.5 | 31.1 | 31.3 | 0.17 |
| 10.0 | 31.6 | 31.8 | 31.3 | 31.6 | 0.21 |
| 11.0 | 31.9 | 32.0 | 31.7 | 31.9 | 0.12 |
| 10.0 | 31.7 | 31.8 | 31.6 | 31.7 | 0.08 |
| 9.0 | 31.5 | 31.7 | 31.5 | 31.6 | 0.09 |
| 8.0 | 31.4 | 31.5 | 31.4 | 31.4 | 0.05 |
| 7.0 | 31.3 | 31.4 | 31.2 | 31.3 | 0.08 |
| 6.0 | 31.2 | 31.2 | 31.0 | 31.1 | 0.09 |
| 5.0 | 31.0 | 30.9 | 30.8 | 30.9 | 0.08 |
| 4.0 | 30.6 | 30.8 | 30.5 | 30.6 | 0.12 |
| 3.0 | 30.4 | 30.4 | 30.2 | 30.3 | 0.09 |
| 2.5 | 30.2 | 30.1 | 29.7 | 30.0 | 0.22 |

FIG. 5E

| OD Discrepancy | | | | | |
|---|---|---|---|---|---|
| Pressure (psig) | Cath 161 O.D Disc. (mm) | Cath 162 O.D Disc. (mm) | Cath 163 O.D Disc. (mm) | Avg. O.D Disc. (mm) | Std. Dev (mm) |
| 2.5 | 0.7 | 0.7 | 1.0 | 0.8 | 0.14 |
| 3 | 0.6 | 0.6 | 1.2 | 0.8 | 0.28 |
| 4 | 0.4 | 0.5 | 0.9 | 0.6 | 0.22 |
| 5 | 0.6 | 0.4 | 0.6 | 0.5 | 0.09 |
| 6 | 0.5 | 0.5 | 0.4 | 0.5 | 0.05 |
| 7 | 0.4 | 0.4 | 0.5 | 0.4 | 0.05 |
| 8 | 0.2 | 0.3 | 0.5 | 0.3 | 0.12 |
| 9 | 0.1 | 0.2 | 0.4 | 0.2 | 0.12 |
| 10 | 0.1 | 0.0 | 0.3 | 0.1 | 0.12 |

FIG. 5F

SYSTEM AND METHOD FOR BALLOON DIAMETER HYSTERESIS COMPENSATION

CROSS-REFERENCE TO RELATED APPLICATION

This application claims priority to Provisional Application No. 62/666,230, filed May 3, 2018, which is herein incorporated by reference in its entirety.

TECHNICAL FIELD

The present disclosure relates to medical devices and methods for treating cardiac arrhythmias. More specifically, the disclosure relates to devices and methods for cardiac cryoablation.

BACKGROUND

Cardiac arrhythmias involve an abnormality in the electrical conduction of the heart and are a leading cause of stroke, heart disease, and sudden cardiac death. Treatment options for patients with arrhythmias include medications and/or the use of medical devices, which can include implantable devices and/or catheter ablation of cardiac tissue, to name a few. In particular, catheter ablation involves delivering ablative energy to tissue inside the heart to block aberrant electrical activity from depolarizing heart muscle cells out of synchrony with the heart's normal conduction pattern. The procedure is performed by positioning the tip of an energy delivery catheter adjacent to diseased or targeted tissue in the heart. The energy delivery component of the system is typically at or near the most distal (i.e. farthest from the user or operator) portion of the catheter, and often at the tip of the catheter.

Various forms of energy can be used to ablate diseased heart tissue. These can include cryoablation procedures which use cryogenic fluid within cryoballoons (also sometimes referred to herein as "balloon catheters"), radio frequency (RF), ultrasound and laser energy, to name a few. During a cryoablation procedure, with the aid of a guide wire, the distal tip of the catheter is positioned adjacent to targeted cardiac tissue, at which time energy is delivered to create tissue necrosis, rendering the ablated tissue incapable of conducting electrical signals. The dose of the energy delivered is a critical factor in increasing the likelihood that the treated tissue is permanently incapable of conduction. At the same time, delicate collateral tissue, such as the esophagus, the bronchus, and the phrenic nerve surrounding the ablation zone can be damaged and can lead to undesired complications. Thus, the operator must finely balance delivering therapeutic levels of energy to achieve intended tissue necrosis while avoiding excessive energy leading to collateral tissue injury.

Atrial fibrillation (AF) is one of the most common arrhythmias treated using catheter ablation. In the earliest stages of the disease, paroxysmal AF, the treatment strategy involves isolating the pulmonary veins from the left atrial chamber. Cryoballoon ablation procedures to treat atrial fibrillation have increased in use in the last several years. In part, this stems from the balloon cryotherapy's ease of use, shorter procedure times and improved patient outcomes. Despite these advantages, there remains needed improvement to further improve patient outcomes and to better facilitate real-time physiological monitoring of tissue to optimally titrate energy to perform both reversible "ice mapping" and permanent tissue ablation.

The objective of any device for the treatment of AF is to achieve isolation in all, not just some, of the pulmonary veins. Also, it is understood that complete occlusion of each pulmonary vein with the cryoballoon is required for adequate antral ablation and electrical isolation. Without pulmonary vein occlusion, blood flow over the balloon during ablation decreases the likelihood of sufficient lesion formation. In order to achieve pulmonary vein occlusion with a balloon, the balloon outer diameter should ideally be a little larger than the opening, or ostium, of the pulmonary vein. If the balloon is too small, there can be gaps between the balloon and the pulmonary vein, enabling blood to flow through the gaps. Conversely, if the balloon is too large, a distal surface of the balloon may be improperly positioned due to the presence of other anatomical features so that the balloon is not sealed tightly against the ostium of the pulmonary vein.

In cryogenic balloon catheter systems, it is common that two balloons are used (although a single balloon may also be used) to create a cryo-chamber near the distal tip of the catheter. The balloons are configured such that there is an inner balloon that receives the cryogenic cooling fluid and an outer balloon that surrounds the inner balloon. The outer balloon acts as part of a safety system to capture the cryogenic cooling fluid in the event of a leak from the inner balloon. In a typical cryogenic balloon catheter system, the cryoballoons are relatively non-compliant and are of a single diameter when in the ablation mode. Thus, current cryoballoons are limited in utility because the diameter of the inflated cryoballoon cannot be changed during ablation. However, human pulmonary vein diameter and shape can vary significantly within and between patients. Consequently, current cryoballoons offer an all or nothing capability in treating pulmonary veins in pulmonary vein isolation procedures.

Thus, a cryoballoon that is more adaptable to common variations in human pulmonary vein diameter and shape is desired in order to better achieve pulmonary vein occlusion and isolation in a greater percentage of patients treated. Additionally, in some applications, it is desirable that the change from one balloon outer diameter to another using the same balloon should be achievable multiple times in a predictable fashion. An ideal variable-diameter balloon would offer a useful range of diameters achievable during ablation within a relatively narrow range of inflation pressures constrained by the need for providing a prescribed amount of cryo-energy delivered into the body of the patient by a cryoablation balloon catheter. This feature would enable the operator to move the balloon catheter from one pulmonary vein to the next, change the outer diameter of the balloon to occlude the pulmonary vein, apply therapy to achieve a successful outcome, and then move to the next pulmonary vein to repeat the process.

SUMMARY

In one example, a balloon catheter system comprising a balloon catheter, a fluid source and a control system. The balloon catheter includes a balloon having a balloon interior, the balloon configured to undergo one or more inflation cycles. The fluid source contains a fluid that is selectively delivered to the balloon interior. The control system is configured to control the delivery of the fluid to the balloon interior at a first inflation pressure to achieve a first targeted balloon diameter, the first inflation pressure being selected by the control system based on a number of inflation cycles undergone by the balloon.

In another example, a balloon catheter system for use by an operator for treating a targeted vein, the balloon catheter system comprising a balloon catheter, a fluid source and a control system. The balloon catheter includes a balloon having a balloon interior, the balloon configured to undergo one or more inflation cycles. The fluid source contains a cryogenic fluid that is selectively delivered to the balloon interior. The control system is configured to selectively control the delivery of the fluid to the balloon interior and to that selectively adjusts an inflation pressure to of the balloon interior based on a number of inflation cycles undergone by the balloon so as to selectively adjust an inflated balloon diameter of the balloon.

In still another example, a method of controlling an inflated diameter of a balloon of a cryoablation catheter balloon of a cryoablation catheter system, the method comprising selectively controlling a delivery of a cryogenic fluid to an interior of the cryoballoon based on a number of inflation cycles undergone by the cryoballoon.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

BRIEF DESCRIPTION OF THE DRAWINGS

FIG. 5E is a table of one representative embodiment showing hysteresis measurements including outside diameter as a function of pressure; and FIG. 5F is a graph of one representative embodiment showing outside diameter discrepancy including outside diameter discrepancy as a function of pressure.

Figure 1:
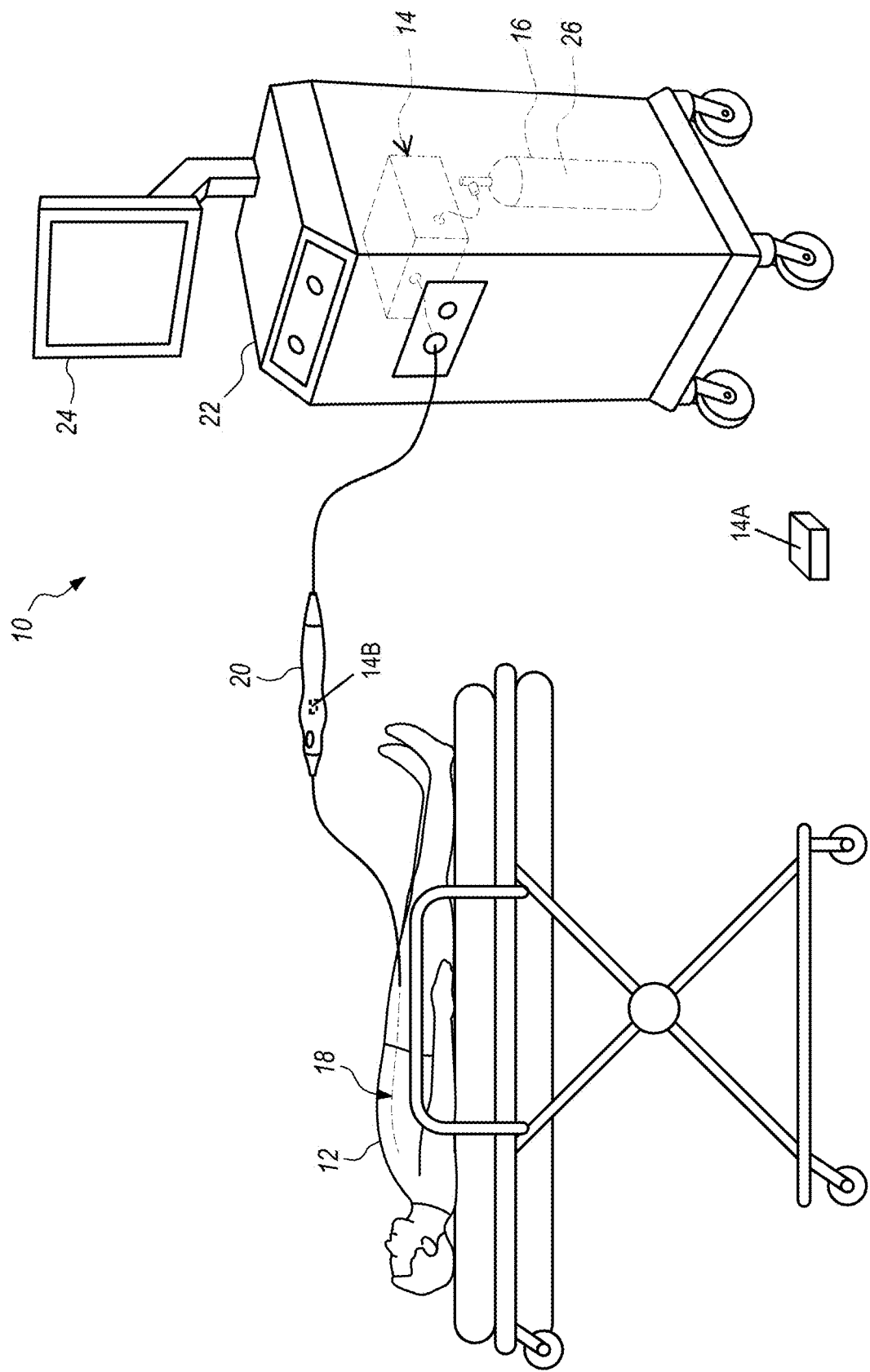
FIG. 1 is a simplified schematic side view illustration of a patient and one embodiment of a cryogenic balloon catheter system having features of the present disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Embodiments of the present disclosure are described herein in the context of a system and method to compensate for balloon diameter hysteresis, e.g., within a cryogenic balloon catheter system. More specifically, in various embodiments, the system and method used within the cryogenic balloon catheter system are configured to utilize empirical data to ensure that an appropriate diameter of the balloon can be provided in a predictable manner within a desired narrow inflation pressure range, regardless of the number of cycles to which the balloon has been subjected. Additionally, or in the alternative, the system and method can enable the operator to selectively increase or decrease the balloon pressure, which selectively adjusts the balloon diameter, for achieving desired vein occlusion. In such embodiments, the specific balloon diameter need not always be known to the operator, so long as the balloon is able to achieve the desired vein occlusion.

Those of ordinary skill in the art will realize that the following detailed description of the present disclosure is illustrative only and is not intended to be in any way limiting. Other embodiments of the present disclosure will readily suggest themselves to such skilled persons having the benefit of this disclosure. Reference will now be made in detail to implementations of the present disclosure as illustrated in the accompanying drawings.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application-related and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Although the disclosure provided herein focuses mainly on cryogenics, it is understood that various other forms of energy can be used to ablate diseased heart tissue. These can include radio frequency (RF), ultrasound and laser energy, as non-exclusive examples. The present disclosure is intended to be effective with any or all of these and other forms of energy.

FIG. 1 is a simplified schematic side view illustration of an embodiment of a cryogenic balloon catheter system 10 for use with a patient 12, which can be a human being or an animal. The design of the cryogenic balloon catheter system 10 can be varied. In certain embodiments, such as the embodiment illustrated in FIG. 1, the cryogenic balloon catheter system 10 can include one or more of a control system 14 (illustrated in phantom), a fluid source 16 (illustrated in phantom), a balloon catheter 18, a handle assembly 20, a control console 22, and a graphical display 24.

It is understood that although FIG. 1 illustrates the structures of the cryogenic balloon catheter system 10 in a particular position, sequence and/or order, these structures can be located in any suitably different position, sequence and/or order than that illustrated in FIG. 1. It is also understood that the cryogenic balloon catheter system 10 can include fewer or additional components than those specifically illustrated and described herein.

In various embodiments, the control system 14 is configured to monitor and control various processes of the ablation procedure. More specifically, the control system 14 can monitor and control release and/or retrieval of a cooling fluid 26 (e.g., a cryogenic fluid) to and/or from the balloon catheter 18. The control system 14 can also control various structures that are responsible for maintaining and/or adjusting a flow rate and/or pressure of the cryogenic fluid 26 that is released to the balloon catheter 18 during the cryoablation procedure. In such embodiments, the cryogenic balloon catheter system 10 delivers ablative energy in the form of cryogenic fluid 26 to cardiac tissue of the patient 12 to create tissue necrosis, rendering the ablated tissue incapable of conducting electrical signals. Additionally, in various embodiments, the control system 14 can control activation and/or deactivation of one or more other processes of the balloon catheter 18. Further, or in the alternative, the control system 14 can receive data and/or other information (hereinafter sometimes referred to as "sensor output") from various structures within the cryogenic balloon catheter system 10. In some embodiments, the control system 14 can receive, monitor, assimilate and/or integrate the sensor output and/or any other data or information received from any structure within the cryogenic balloon catheter system 10 in order to control the operation of the balloon catheter 18. As provided herein, in various embodiments, the control system 14 can initiate and/or terminate the flow of cryogenic fluid 26 to the balloon catheter 18 based on the sensor output. Still further, or in the alternative, the control system 14 can control positioning of portions of the balloon catheter 18 within the body of the patient 12, and/or can control any other suitable functions of the balloon catheter 18.

Additionally, in various embodiments, as provided in greater detail herein below, the control system 14 can utilize stored empirical data to apply known inflation pressures to the balloon catheter 18 to achieve known and targeted balloon diameters within the balloon catheter 18 regardless of the number of inflation cycles to which the balloon has been subjected. Stated in another manner, the control system 14 can receive and/or store the empirical data and can utilize such empirical data to compensate for balloon hysteresis, which in this context entails the need to utilize varying inflation pressure levels to achieve the desired balloon diameter through multiple inflation cycles.

Further, in some embodiments, the control system 14 can include and/or incorporate the use of a pressure controller 14A, that can be provided remotely from the control console 22. The pressure controller 14A can be utilized by the operator to selectively adjust and/or control the inflation pressure within the balloon catheter 18, e.g., within a balloon of the balloon catheter 18, in order to selectively adjust the balloon diameter. In certain such embodiments, the pressure controller 14A can be provided in the form of a handheld remote device or a foot pedal, that can be selectively manipulated by the operator. Alternatively, the pressure controller 14A can be provided in another suitable form. For example, in one non-exclusive alternative embodiment, the pressure controller 14A can be provided within the graphical display 24. Still further, in some such embodiments, the control system 14 can further include, incorporate or utilize a pressure sensor 14B that can be configured to sense a contact pressure between the balloon and the targeted vein to be occluded. As provided herein, the pressure sensor 14B can be utilized to better ensure that a desired, predetermined contact force or contact pressure is generated between the balloon and the targeted vein to achieve the desired vein occlusion. It is appreciated that the pressure sensor 14B can be positioned in any suitable manner within the cryogenic balloon catheter system 10.

Still further, it is also appreciated that the embodiments that utilize the pressure controller 14A and/or the pressure sensor 14B can also include the control system 14 utilizing the unique empirical data as described in detail herein.

The fluid source 16 contains the cryogenic fluid 26, which is delivered to the balloon catheter 18 with or without input from the control system 14 during a cryoablation procedure. Once the ablation procedure has initiated, the cryogenic fluid 26 can be delivered and the resulting gas, after a phase change, can be retrieved from the balloon catheter 18, and can either be vented or otherwise discarded as exhaust. Additionally, the type of cryogenic fluid 26 that is used during the cryoablation procedure can vary. In one non-exclusive embodiment, the cryogenic fluid 26 can include liquid nitrous oxide. However, any other suitable cryogenic fluid 26 can be used. For example, in one non-exclusive alternative embodiment, the cryogenic fluid 26 can include liquid nitrogen.

The design of the balloon catheter 18 can be varied to suit the specific design requirements of the cryogenic balloon catheter system 10. As shown, the balloon catheter 18 is configured to be inserted into the body of the patient 12 during the cryoablation procedure, i.e. during use of the cryogenic balloon catheter system 10. In one embodiment, the balloon catheter 18 can be positioned within the body of the patient 12 using the control system 14. Stated in another manner, the control system 14 can control positioning of the balloon catheter 18 within the body of the patient 12. Alternatively, the balloon catheter 18 can be manually positioned within the body of the patient 12 by a healthcare professional (also referred to herein as an "operator"). As used herein, a healthcare professional and/or an operator can include a physician, a physician's assistant, a nurse and/or any other suitable person and/or individual. In certain embodiments, the balloon catheter 18 is positioned within the body of the patient 12 utilizing at least a portion of the sensor output that is received by the control system 14. For example, in various embodiments, the sensor output is received by the control system 14, which can then provide the operator with information regarding the positioning of the balloon catheter 18. Based at least partially on the sensor output feedback received by the control system 14, the operator can adjust the positioning of the balloon catheter 18 within the body of the patient 12 to ensure that the balloon catheter 18 is properly positioned relative to targeted cardiac tissue (not shown).

The handle assembly 20 is handled and used by the operator to operate, position and control the balloon catheter 18. The design and specific features of the handle assembly 20 can vary to suit the design requirements of the cryogenic balloon catheter system 10. In the embodiment illustrated in FIG. 1, the handle assembly 20 is separate from, but in electrical and/or fluid communication with the control system 14, the fluid source 16, and the graphical display 24. In some embodiments, the handle assembly 20 can integrate and/or include at least a portion of the control system 14, e.g., the pressure sensor 14B, within an interior of the handle assembly 20. It is understood that the handle assembly 20 can include fewer or additional components than those specifically illustrated and described herein.

In various embodiments, the handle assembly 20 can be used by the operator to initiate and/or terminate the cryoablation process, e.g., to start the flow of the cryogenic fluid 26 to the balloon catheter 18 in order to ablate certain targeted heart tissue of the patient 12. In certain embodiments, the control system 14 can override use of the handle assembly 20 by the operator. Stated in another manner, in some embodiments, the control system 14 can terminate the cryoablation process without the operator using the handle assembly 20 to do so.

The control console 22 is coupled to the balloon catheter 18 and the handle assembly 20. Additionally, in the embodiment illustrated in FIG. 1, the control console 22 includes at least a portion of the control system 14, the fluid source 16, and the graphical display 24. However, in alternative embodiments, the control console 22 can contain additional structures not shown or described herein. Still alternatively, the control console 22 may not include various structures that are illustrated within the control console 22 in FIG. 1. For example, in certain non-exclusive alternative embodiments, the control console 22 does not include the graphical display 24.

In various embodiments, the graphical display 24 is electrically connected to the control system 14. Additionally, the graphical display 24 provides the operator of the cryogenic balloon catheter system 10 with information that can be used before, during and after the cryoablation procedure. For example, the graphical display 24 can provide the operator with information based on the sensor output and any other relevant information that can be used before, during and after the cryoablation procedure. The specifics of the graphical display 24 can vary depending upon the design requirements of the cryogenic balloon catheter system 10, or the specific needs, specifications and/or desires of the operator.

In one embodiment, the graphical display 24 can provide static visual data and/or information to the operator. In addition, or in the alternative, the graphical display 24 can provide dynamic visual data and/or information to the operator, such as video data or any other data that changes over time, e.g., during an ablation procedure. Further, in various embodiments, the graphical display 24 can include one or more colors, different sizes, varying brightness, etc., that may act as alerts to the operator. Additionally, or in the alternative, the graphical display 24 can provide audio data or information to the operator.

Still further, in certain embodiments, the operator can utilize the graphical display 24 to control certain functions of the cryogenic balloon catheter system 10. For example, in some such embodiments, the operator can utilize the graphical display 24, i.e. a pressure controller 14A that is accessible via the graphical display 24, to adjust and/or control the pressure inside the balloon catheter 18.

Figure 2:
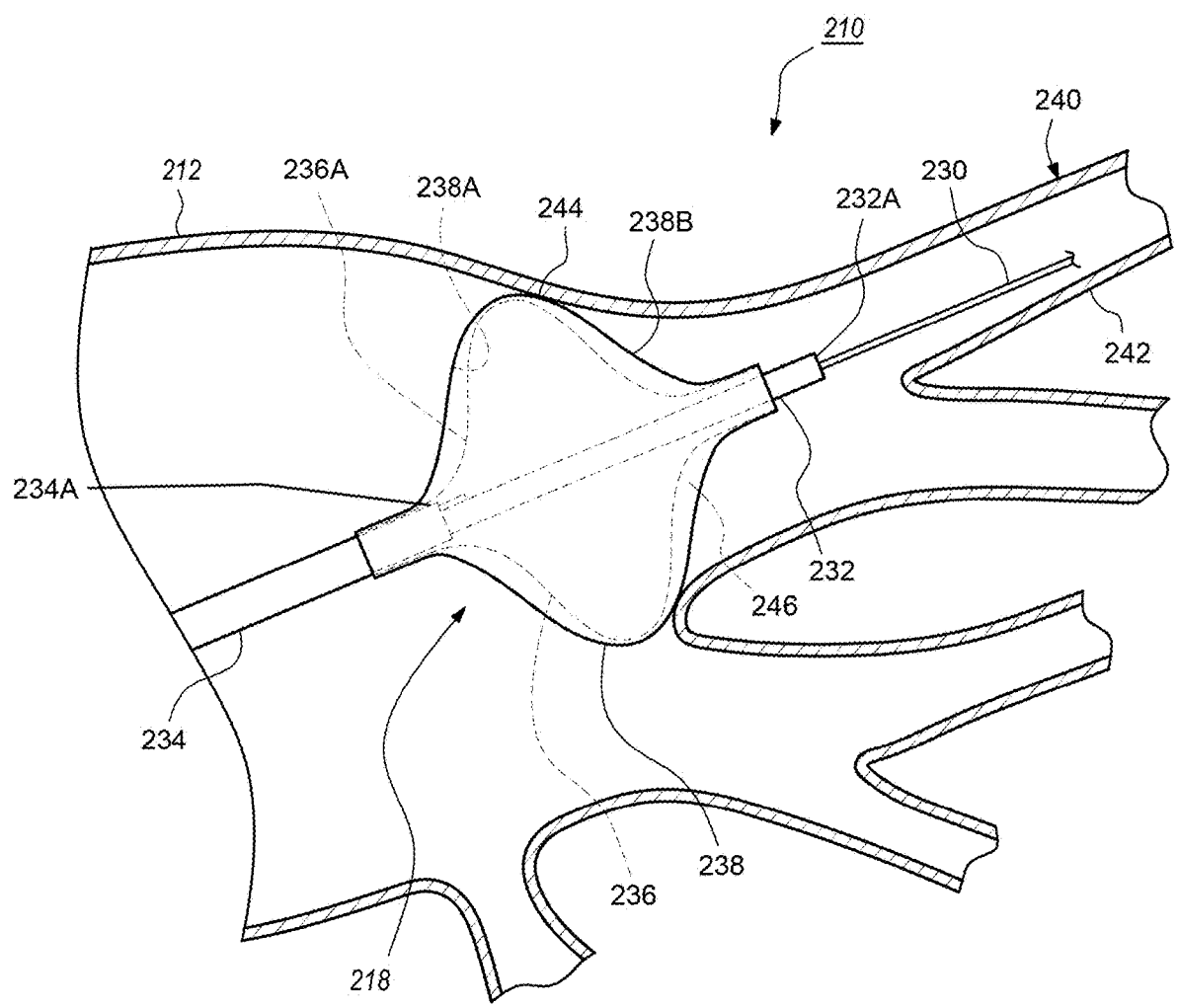
FIG. 2 is a simplified schematic side view of a portion of the patient and a portion of one embodiment of the cryogenic balloon catheter system including a balloon catheter.

FIG. 2 is a simplified schematic side view of a portion of the patient 212 and a portion of one embodiment of the cryogenic balloon catheter system 210. In this embodiment, the cryogenic balloon catheter system 210 includes a balloon catheter 218.

The design of the balloon catheter 218 can be varied to suit the design requirements of the cryogenic balloon catheter system 210. In the embodiment illustrated in FIG. 2, the balloon catheter 218 includes one or more of a guidewire 230, a guidewire lumen 232, a catheter shaft 234, an inner inflatable balloon 236 (sometimes referred to herein as a "first inflatable balloon" or "first balloon") and an outer inflatable balloon 238 (sometimes referred to herein as a "second inflatable balloon" or "second balloon"). As used herein, it is recognized that either balloon 236, 238 can be described as the first balloon or the second balloon. Alternatively, the balloon catheter 218 can be configured to include only a single balloon. Additionally, it is understood that the balloon catheter 218 can include other structures as well. However, for the sake of clarity, these other structures have been omitted from the Figures.

As shown in the embodiment illustrated in FIG. 2, the balloon catheter 218 is configured to be positioned within the circulatory system 240 of the patient 212. The guidewire 230 and guidewire lumen 232 are inserted into a pulmonary vein 242 of the patient 212, and the catheter shaft 234 and the balloons 236, 238 are moved along the guidewire 230 and/or the guidewire lumen 232 to near an ostium 244 of the pulmonary vein 242. As provided herein, one way to treat a wider range of human anatomy is to better size the balloons 236, 238 of the balloon catheter 218 to match the diameter of the pulmonary vein 242. In general, it is the object of the balloon catheter 218 to seal the pulmonary vein 242 so that blood flow is occluded. Only when occlusion is achieved does the cryothermic energy, e.g., of the cryogenic fluid 26 (illustrated in FIG. 1), cause tissue necrosis which, in turn, provides for electrically blocking aberrant electrical signals that trigger atrial fibrillation. Unfortunately, as noted above, human anatomy varies, and the diameter of pulmonary veins varies within a given patient as well as between patients.

As an overview, in various embodiments as described in detail herein, one way to treat the variety of pulmonary vein diameters is to provide a balloon catheter 218 that includes balloons 236, 238 that are selectively adjustable to provide a range of available diameters. Based on the varying diameters of the pulmonary veins in the human body, the ideal range of balloon diameter may range from 26 to 32 mm, although it is understood that the true value for the diameter of any given pulmonary vein can vary outside the normal parameters thus potentially requiring balloon diameters that may be greater than 32 mm or less than 26 mm. Further, it is appreciated that balloon hysteresis will cause the balloons 236, 238 to react somewhat differently to a given inflation pressure as the balloons 236, 238 experience a number of inflation cycles. More particularly, balloon hysteresis as referred to herein entails the concept of a change in the pressure-diameter curve for a given balloon 236, 238 from a first inflation cycle to any subsequent inflation cycles. Accordingly, as provided herein, it is desired to be able to selectively adjust the inflation pressure, e.g., within a balloon interior, to achieve predictable and desired balloon diameters through multiple inflation cycles.

In typical balloons in current use, there is a lack of balloon materials that lend themselves to meet all the performance and safety requirements for a cryoballoon and enable a useful range of diameters. For example, non-compliant balloons (described herein as balloons that are typically insensitive to pressure changes, with an inflated diameter that remains within less than approximately 6% of the nominal diameter over the typical operating range of internal pressures) or semi-compliant balloons (described herein as balloons where the inflated diameter changes between approximately 6-12% from the nominal diameter over the typical operating range of internal pressures) in general use typically do not offer a wide enough range to meet the clinical need. Conversely, while compliant balloons (described herein as balloons where the inflated diameter changes greater than approximately 12% from the nominal diameter over the typical operating range of internal pressures) made from very soft polymers expand readily to fit the anatomy, they are plagued by hysteresis and have low burst pressures that fail to offer appropriate levels of safety. In order to effectively offer a range of diameters needed to treat a wide range of human pulmonary vein anatomy, the balloons 236, 238 will typically require compliance that falls between a traditionally defined compliant balloon and semi-compliant balloon.

Thus, in various embodiments, the balloon catheter 218 can include an inner inflatable balloon 236 that is less compliant than the outer inflatable balloon 238, and/or that has a larger natural diameter at a nominal working balloon pressure. As used herein, in certain applications, the nominal working balloon pressure can be between approximately 1.5 psi and 3.5 psi. More specifically, in one application, the nominal working balloon pressure can be approximately 2.5 psi. Alternatively, in other applications, the nominal working balloon pressure can be greater than 3.5 psi or less than 1.5 psi.

For example, in some such embodiments, the inner inflatable balloon 236 can be non-compliant or semi-compliant and have a diameter that is between approximately 29 mm and 35 mm at a nominal working balloon pressure, and the outer inflatable balloon 238 can be compliant and have a diameter that is between approximately 23 mm and 29 mm at a nominal working balloon pressure. As noted, in certain embodiments, to work effectively as desired, it is merely important that the inner inflatable balloon 236 be less compliant than the outer inflatable balloon 238, and/or that the inner inflatable balloon 236 have a larger diameter at a nominal working balloon pressure than the outer inflatable balloon 238.

In certain non-exclusive embodiments, the inner inflatable balloon 236 can have a diameter at a nominal working balloon pressure that is between approximately 0% and 30% greater than a diameter of the outer inflatable balloon 238 at a nominal working balloon pressure. For example, the inner inflatable balloon 236 can have a diameter at a nominal working balloon pressure that is approximately 1%, 2%, 3%, 5%, 7%, 10%, 12%, 15%, 17%, 20%, 22%, 25%, 27% or 30% greater than a diameter of the outer inflatable balloon 238 at a nominal working balloon pressure. Alternatively, the inner inflatable balloon 236 can have a diameter at a nominal working balloon pressure that is more than 30% greater than a diameter of the outer inflatable balloon 238 at a nominal working balloon pressure.

Additionally, in some non-exclusive embodiments, the inner inflatable balloon 236 can be non-compliant or semi-compliant and have a compliance over working range of at least approximately 1%, 2%, 3%, 4%, 5%, 6%, 7%, 8%, 9%, 10%, 11% or 12%. Alternatively, the inner inflatable balloon 236 can be compliant and have a compliance over working range of at least approximately 13%, 14%, 15%, 16%, 17%, 18%, 19% or 20%. Further, in certain non-exclusive embodiments, the outer inflatable balloon 238 can be semi-compliant or compliant and have a compliance over working range of at least approximately 6%, 7%, 8%, 9%, 10%, 11%, 12%, 13%, 14%, 15%, 16%, 17%, 18%, 19% or 20%. Alternatively, the outer inflatable balloon 238 can be compliant and have a compliance over working range of at least approximately 21%, 22%, 23%, 24%, 25%, 26%, 27%, 28%, 29% or 30%.

Moreover, in some non-exclusive embodiments, the outer inflatable balloon 238 can have a compliance that is between approximately 1% and 20% greater than a compliance of the inner inflatable balloon 236. For example, in such embodiments, the outer inflatable balloon 238 can have a compliance that is at least approximately 1%, 2%, 3%, 4%, 5%, 6%, 7%, 8%, 9%, 10%, 11%, 12%, 13%, 14%, 15%, 16%, 17%, 18%, 19% or 20% greater than a compliance of the inner inflatable balloon 236. Alternatively, the outer inflatable balloon 238 can have a compliance that is more than 20% greater than a compliance of the inner inflatable balloon 236.

In such embodiments, by combining a less compliant inner inflatable balloon 236 that is large, e.g., 32 mm at a nominal working balloon pressure of approximately 2.5 psi for example, and a smaller, more compliant outer inflatable balloon 238, e.g., 26 mm at a nominal working balloon pressure of approximately 2.5 psi, the outer inflatable balloon 238 constrains expansion of the inner inflatable balloon 238. Such a combination further enables a balloon catheter 218 with a wide range of inflated diameters within a small range of working pressures to ensure safe, low-pressure operation that reduces the likelihood of a balloon rupture.

With such design, the range of available diameters that can be achieved is increased. In addition, constraining the upper diameter limit of the two-balloon system with the less compliant inner inflatable balloon 236 effectively puts a ceiling on diameter increase. Further, the inner inflatable balloon 236 has a higher burst pressure and contributes more in protecting against an inadvertent burst.

As illustrated, the inner inflatable balloon 236 is positioned substantially, if not completely, within the outer inflatable balloon 238. It is appreciated that the naturally larger inner inflatable balloon 236 may have to be folded or otherwise manipulated to fit within the naturally smaller outer inflatable balloon 238. However, as the balloons 236, 238 are inflated, e.g., as the inner inflatable balloon 236 is directly inflated, which then indirectly inflates the outer inflatable balloon 238, such folds or manipulations of the inner inflatable balloon 236 do not adversely impact the desired operation of the inner inflatable balloon 236.

As noted, the smaller outer inflatable balloon 238 constrains the inner inflatable balloon 236 from expanding to its nominal size at low pressures by being formed smaller in diameter. Only at higher pressures does the hoop stress inside the balloon overcome the constraining forces of the outer inflatable balloon 238 to increase the diameter of the two-balloon system. Optimally, the characteristics of each of the inner inflatable balloon 236 and the outer inflatable balloon 238, including diameter, balloon wall thickness, and balloon material selection are chosen to minimize balloon hysteresis, provide for an adequate range of expansion, and offer a high burst pressure relative to the working pressure range of the cryogenic balloon catheter system 210. Additionally, as provided herein, the control system 14 (illustrated in FIG. 1) can be configured to utilize empirical data, e.g., from any previous testing or usage of the balloons 236, 238 or balloons of similar size, shape and design, to compensate for any balloon hysteresis that may be present within the balloons 236, 238 of the balloon catheter 218. Further, in some embodiments, as noted herein, the control system 14 can incorporate the use of a pressure controller 14A (illustrated in FIG. 1) and/or a pressure sensor 14B (illustrated in FIG. 1) to enable the operator to selectively adjust the inflation pressure within the balloons 236, 238. Moreover, the selective adjustment of the inflation pressure necessarily adjusts the balloon diameter in order to achieve desired vein occlusion, even if the specific balloon diameter remains unknown to the operator.

The specific design of and materials used for each of the inner inflatable balloon 236 and the outer inflatable balloon 238 can be varied.

In certain embodiments, the inner inflatable balloon 236 can be made from relatively non-compliant or semi-compliant materials. Additionally, the inner inflatable balloon 236 will typically be formed to the high end of a working diameter range. For example, in one non-exclusive embodiment, for a cryogenic balloon catheter system 210 capable of spanning from 26 mm to 32 mm, the diameter of the inner inflatable balloon 236 at a nominal working balloon pressure can be approximately 32 mm, though it may be more or less to achieve desirable diameter ranges and accommodate post balloon forming processes such as sterilization which may shrink the balloon. Further, in some embodiments, the inner inflatable balloon 236 is bonded to a distal end 234A of the catheter shaft 234 and near a distal end 232A of the guidewire lumen 232. A variety of bonding techniques can be used and include heat bonding and adhesive bonding.

Some representative materials suitable for the inner inflatable balloon 236 for this variable-diameter compliant two-balloon system include various grades of polyether block amides (PEBA) such as the commercially available PEBAX® (marketed by Arkema, Colombes, France), or a polyurethane such as Pellathane™ (marketed by Lubrizol). Additionally, or in the alternative, the materials can include PET (polyethylene terephthalate), nylon, polyurethane, and other co-polymers of these materials, as non-exclusive examples. In another embodiment, a polyester block copolymer known in the trade as Hytrel® (DuPont™) is also a suitable material for the inner inflatable balloon 236. Further, the materials may be mixed in varying amounts to fine tune properties of the inner inflatable balloon 236. As noted, the inner inflatable balloon 236 can be relatively inelastic in comparison to the outer inflatable balloon 238. As illustrated, the outer inflatable balloon 238 substantially encircles the inner inflatable balloon 236. Additionally, in certain embodiments, the outer inflatable balloon 238 can be made from a relatively compliant material. Further, the outer inflatable balloon 238 will typically be formed to the low end of the balloon diameter working range. For example, in one non-exclusive embodiment, for a cryogenic balloon catheter system 210 capable of spanning from 26 mm to 32 mm, the diameter of the outer inflatable balloon 238 at a nominal working balloon pressure can be approximately 26 mm, though the diameter may be more or less to achieve a desirable range of balloon diameters within a specified pressure range. The outer inflatable balloon 238 may be bonded to a neck of the inner inflatable balloon 236 or to the distal end 234A of the catheter shaft 234. The other end of the outer inflatable balloon 238 may be bonded to the guidewire lumen 232 and/or to a portion of the inner inflatable balloon 236. A variety of bonding techniques can be used and include heat bonding and adhesive bonding.

Some representative materials suitable for the outer inflatable balloon 238 for this variable-diameter compliant two-balloon system include various grades of polyether block amides (PEBA) such as the commercially available PEBAX® (marketed by Arkema, Colombes, France), or a polyurethane such as Pellathane™ (marketed by Lubrizol). Additionally, or in the alternative, the materials can include aliphatic polyether polyurethanes in which carbon atoms are linked in open chains, including paraffins, olefins, and acetylenes. Another suitable material goes by the trade name Tecoflex® (marketed by Lubrizol). Other available polymers from the polyurethane class of thermoplastic polymers with exceptional elongation characteristics are also suitable for use as the outer inflatable balloon 238. Further, the materials may be mixed in varying amounts to fine tune properties of the outer inflatable balloon 238.

A lubricious biocompatible material such as a grease may be inserted between the balloons to enable free expansion against the constraining outer balloon. Other lubricants are contemplated. Alternatively, a lubricious additive may be compounded into either the inner balloon or outer balloon tubing to reduce friction between the two balloons during inflation to better enable predictable and repeatable balloon diameters for a given pressure. The lubricant increases the likelihood that the intended balloon diameter is achieved at the various pressures defining the working range, such as 26 to 32 mm inflated balloon diameter. The lubricant can also reduce the working pressures, as far as is possible, so that the full working range of balloon diameter may be several multiples below the burst pressure of the two-balloon system. For example, a two-balloon compliant balloon system may have an average burst pressure of 30 psi. A working range of pressures such as 2.5 psi to 11 psi ensures that there is a significant margin of safety between the balloon burst pressure and the pressure range needed to provide the full span of balloon diameters that the operator may desire.

After the two balloons 236, 238 are bonded to the catheter shaft 234, the cryogenic balloon catheter system 210 can be completed. After assembly, the balloons 236, 238 may be subjected to at least one inflation cycle to reduce hysteresis in the system. The completed device is then sterilized using ETO gas, for example. Additionally, in one embodiment, either of the balloons 236, 238, may be rendered electrically conductive by doping the material from which it is made with a conductive metal or other conductive substance. In such embodiment, the electrically conductive balloons can be particularly suitable for the outer inflatable balloon 238.

During use, the inner inflatable balloon 236 can be partially or fully inflated so that at least a portion of the inner inflatable balloon 236 expands against at least a portion of the outer inflatable balloon 238. Stated in another manner, during use of the balloon catheter 218, at least a portion of an outer surface 236A of the inner inflatable balloon 236 expands and is positioned substantially directly against a portion of an inner surface 238A of the outer inflatable balloon 238. At certain times during usage of the cryogenic balloon catheter system 210, the inner inflatable balloon 236 and the outer inflatable balloon 238 define an inter-balloon space 246, or gap, between the balloons 236, 238. The inter-balloon space 246 is illustrated between the inner inflatable balloon 236 and the outer inflatable balloon 238 in FIG. 2 for clarity, although it is understood that at certain times during usage of the cryogenic balloon catheter system 210, the inter-balloon space 246 has very little or no volume. As provided herein, once the inner inflatable balloon 236 is sufficiently inflated, an outer surface 238B of the outer balloon 238 can then be positioned within the circulatory system 240 of the patient 212 to abut and/or substantially form a seal with the ostium 244 of the pulmonary vein 242 to be treated.

Additionally, as noted above, in certain embodiments, the control system 14 can be configured to utilize empirical data, e.g., from any previous testing or usage of the balloons 236, 238 or balloons of similar size, shape and design, to compensate for any balloon hysteresis that may be present within the balloons 236, 238 of the balloon catheter 218. More specifically, the control system 14 can utilize such unique-empirical data to apply known inflation pressures to the balloons 236, 238, e.g., within a balloon interior of the balloons 236, 238, to achieve known and targeted balloon diameters within the balloons 236, 238 regardless of the number of inflation cycles to which the balloons 236, 238 have been subjected. As such, the control system 14 will compensate for balloon hysteresis, which, as noted, entails the need to utilize varying inflation pressure levels to achieve the desired balloon diameter through multiple inflation cycles. It is again noted that in certain alternative embodiments the balloon catheter 218 can be configured to include only a single balloon. In such embodiments, the control system 14 will be configured to compensate for balloon diameter hysteresis in only the single balloon.

It is appreciated that the empirical data-based control scheme utilized within the control system 14 can be created for balloons 236, 238 made from any of various materials and/or of any shapes in sizes. Thus, the use of such control schemes by the control system 14 to compensate for balloon hysteresis is envisioned in various embodiments, including such embodiment where the size, shape and materials do not necessarily follow the preferred guidelines as set forth herein above.

In various embodiments, the factors to be utilized can include one or more of balloon materials, balloon dimensions (e.g., before an initial inflation), inflation pressure, and number of inflations to which the balloons have been subjected. Additionally, or in the alternative, the factors can include other factors such as ambient environmental conditions (e.g., ambient temperature, ambient pressure, etc.), and/or any other suitable factors.

As an overview, in such embodiments, during use of the cryogenic balloon catheter system 210, the control system 14 can utilize the empirical data to set the required balloon inflation pressure based on the previously collected empirical data, and apply known inflation pressures to achieve known and targeted balloon diameters, regardless of the cycle number for the balloons 236, 238. In this manner, the control system 14 can provide the appropriate inflation pressure to the balloons 236, 238, e.g., within the balloon interior, regardless of the number of inflation cycles to which the balloon catheter 218 was previously subjected, to achieve a targeted balloon diameter.

It is appreciated that the hysteresis and/or compliance of a balloon can be measured. Additionally, the measurement can be performed at any time after the forming of the balloon. For example, the balloon hysteresis and/or compliance can be measured after the balloon is bonded onto the catheter shaft. The balloon hysteresis and/or compliance can also be measured after the balloon is fully assembled. Further, the balloon hysteresis and/or compliance can be measured after sterilization. In cases where the balloon hysteresis and/or compliance is measured after sterilization, the process can be performed by the operator immediately prior to an ablation procedure or even during an ablation procedure. An inflation cycle can expand the balloon and inelastically deform the balloon using pressure so that subsequent balloon inflation and ablation cycles follow a more repeatable pressure-diameter curve. Additionally, in cases where the balloon is inflated prior to the ablation procedure, the operator will typically prepare the balloon by submerging it into a tub of sterile saline solution to shake off bubbles attached to the balloon in the folds.

Further, as provided herein, in other embodiments, the cryogenic balloon catheter system 210 can be configured to enable the operator to selectively adjust the inflation pressure within the balloons 236, 238 to selectively adjust the balloon diameter. Thus, the operator can utilize the control system 14 and/or the pressure controller 14A to selectively adjust the balloon diameter, e.g., when moving from vein to vein and/or when repositioning the balloon catheter 218, to better match the diameter of the pulmonary veins which can vary widely within a patient and between patients. For example, in some such embodiments, the operator can selectively increase the inflation pressure within the balloons 236, 238 to create an increase in the balloon diameter; and the operator can selectively decrease the inflation pressure within the balloons 236, 238 to create a decrease in the balloon diameter. It is appreciated that the increase or decrease of the balloon diameter in this manner can be accomplished without the operator necessarily knowing what the balloon diameter actually is at any given time.

In certain such embodiments, as noted above, the pressure controller 14A can be provided to the operator as part of the graphical display 24 (illustrated in FIG. 1). For example, in one non-exclusive embodiment, the pressure controller 14A can be provided in the form of a slider that allows for selective adding to or subtracting from the inflation pressure (e.g., plus and minus buttons) that sends a signal to increase or decrease the inflation pressure within the balloons 236, 238.

Alternatively, in other such embodiments, the pressure controller 14A can be provided to the operator in the form of a remote control device, such as a handheld remote control device or a foot pedal, that when manipulated by the operator will send a signal to correspondingly increase or decrease the inflation pressure within the balloons 236, 238.

In some embodiments, the control system 14 and/or the pressure controller 14A can incorporate a setting that merely requests that vein occlusion be optimized (a "vein occlusion optimization" setting). Such embodiments can further include the use of a pressure sensor 14B that is configured to sense a contact force between the balloons 236, 238 and the targeted vein to be occluded. With use of such setting, when selected by the operator, the control system 14 and/or the pressure controller 14A will send a signal to increase or decrease the inflation pressure as necessary until a predetermined desired contact force is sensed by the pressure sensor 14B that is indicative of the achievement of desired vein occlusion.

Figures 3A, 3B:
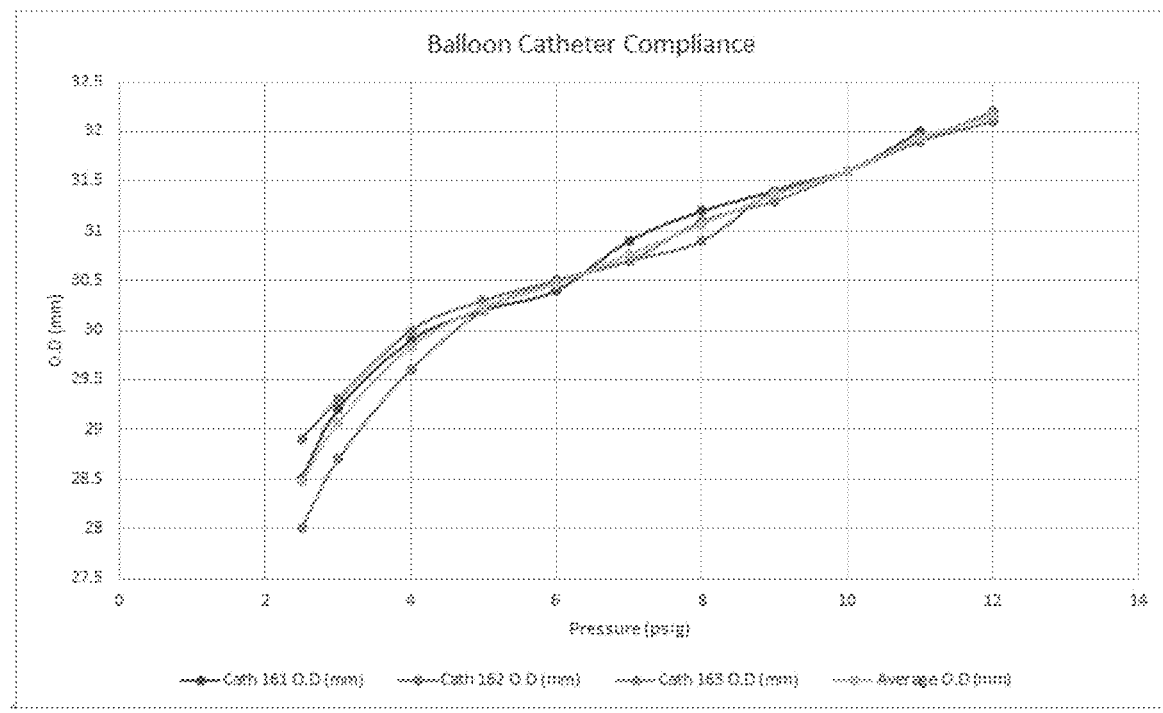
FIG. 3A is a graph of one representative embodiment showing balloon catheter compliance including outside diameter as a function of pressure.
FIG. 3B is a table of one representative embodiment showing balloon catheter compliance including outside diameter as a function of pressure.

FIG. 3A is a graph of one representative embodiment showing balloon catheter compliance including outside diameter (in millimeters) as a function of pressure (in psig).

FIG. 3B is a table of one representative embodiment showing balloon catheter compliance including outside diameter (in millimeters) as a function of pressure (in psig).

Figure 4A:
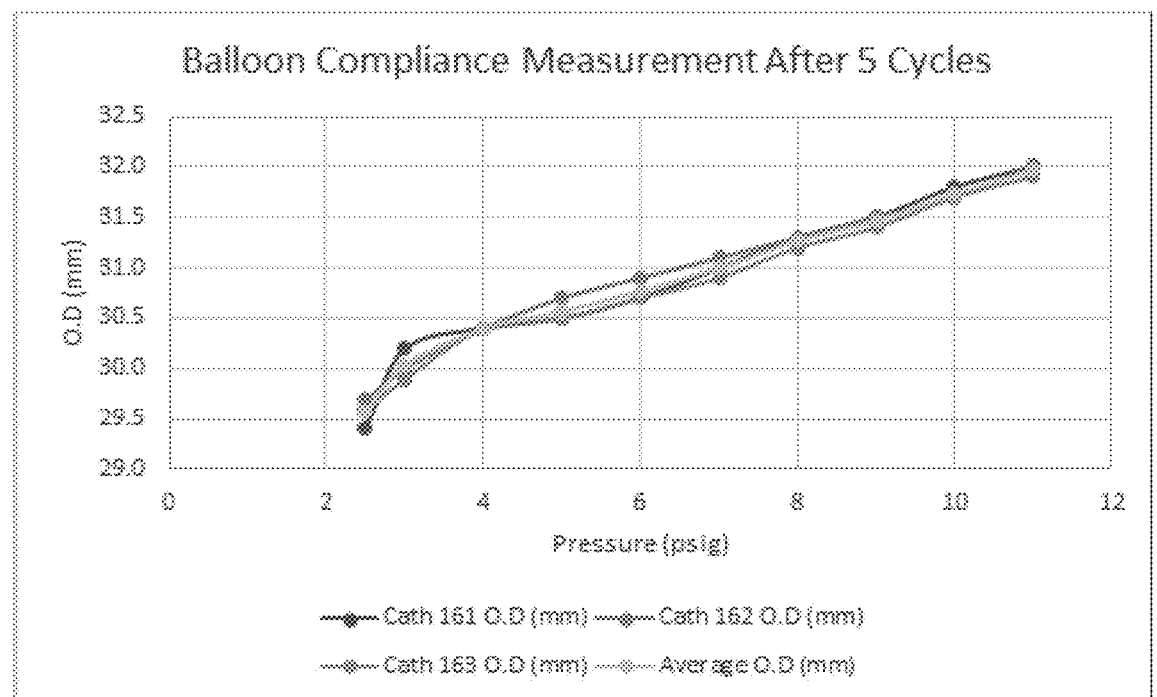
FIG. 4A is a graph of one representative embodiment showing balloon compliance measurement after five cycles including outside diameter as a function of pressure.

FIG. 4A is a graph of one representative embodiment showing balloon compliance measurement after five cycles including outside diameter (in millimeters) as a function of pressure (in psig).

Figure 4B:
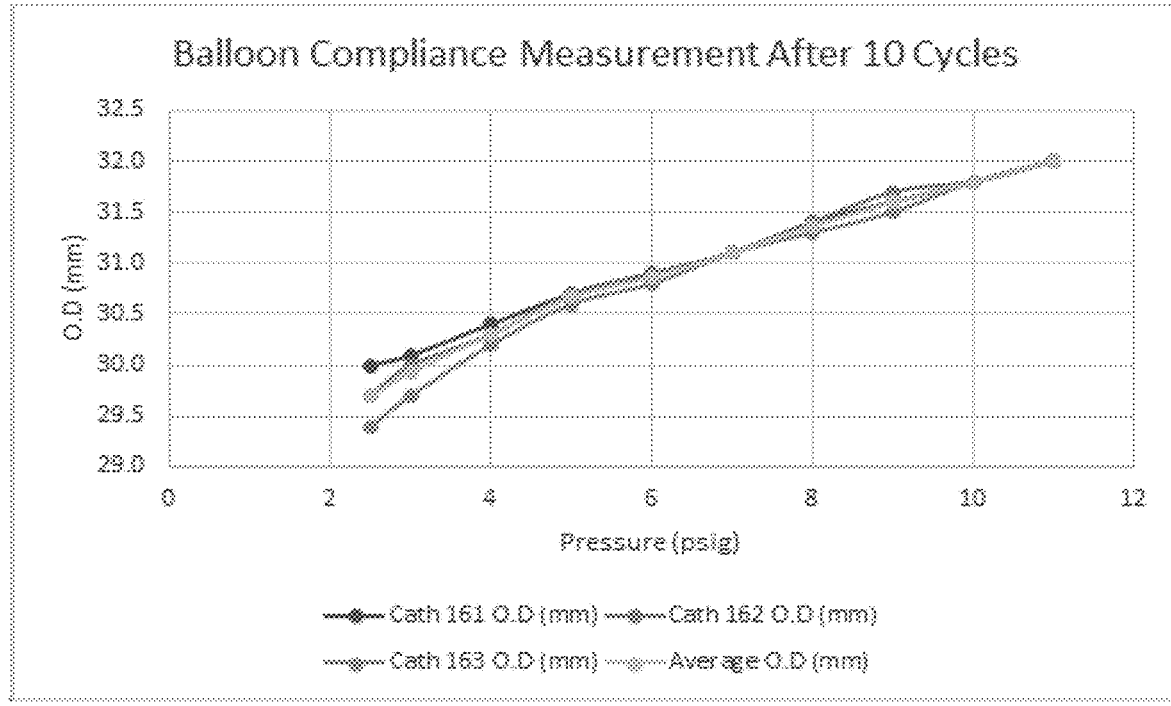
FIG. 4B is a graph of one representative embodiment showing balloon compliance measurement after ten cycles including outside diameter as a function of pressure.

FIG. 4B is a graph of one representative embodiment showing balloon compliance measurement after ten cycles including outside diameter (in millimeters) as a function of pressure (in psig).

Figures 4C, 4D:
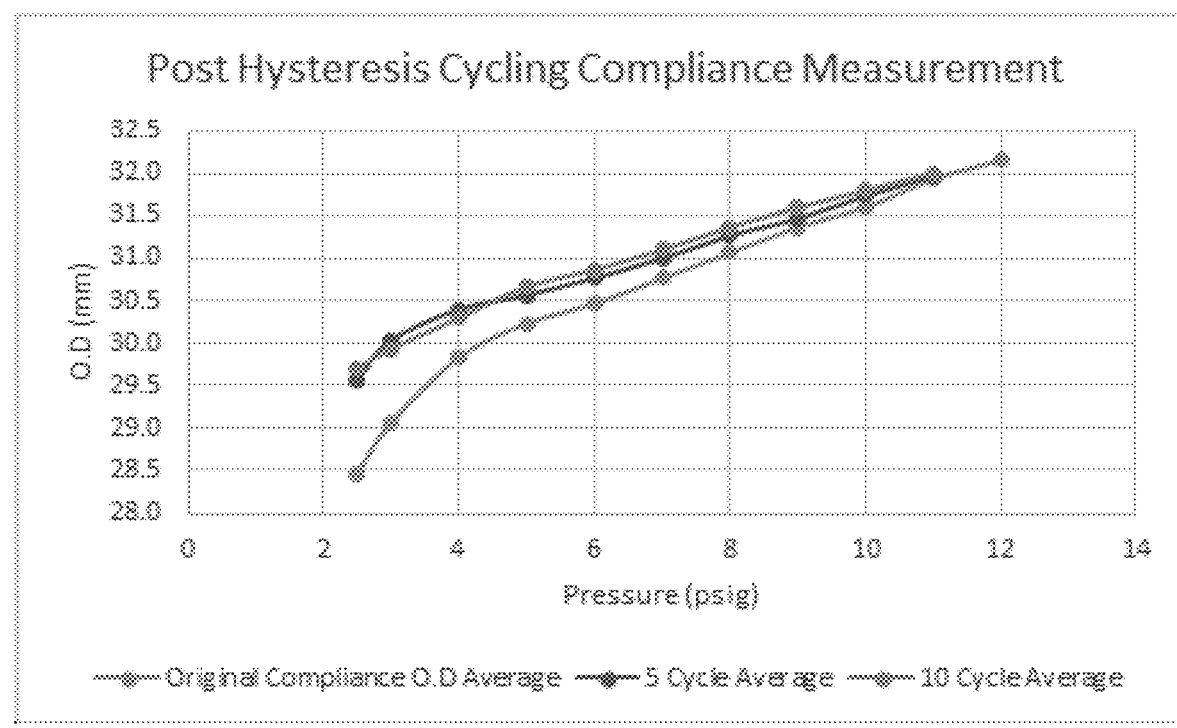
FIG. 4C is a graph of one representative embodiment showing post hysteresis cycling compliance measurement including outside diameter as a function of pressure.
FIG. 4D is a table of one representative embodiment showing standard deviation for cycling compliance.

FIG. 4C is a graph of one representative embodiment showing post hysteresis cycling compliance measurement including outside diameter (in millimeters) as a function of pressure (in psig).

FIG. 4D is a table of one representative embodiment showing standard deviation (in millimeters) for cycling compliance (in psig).

Figure 5A:
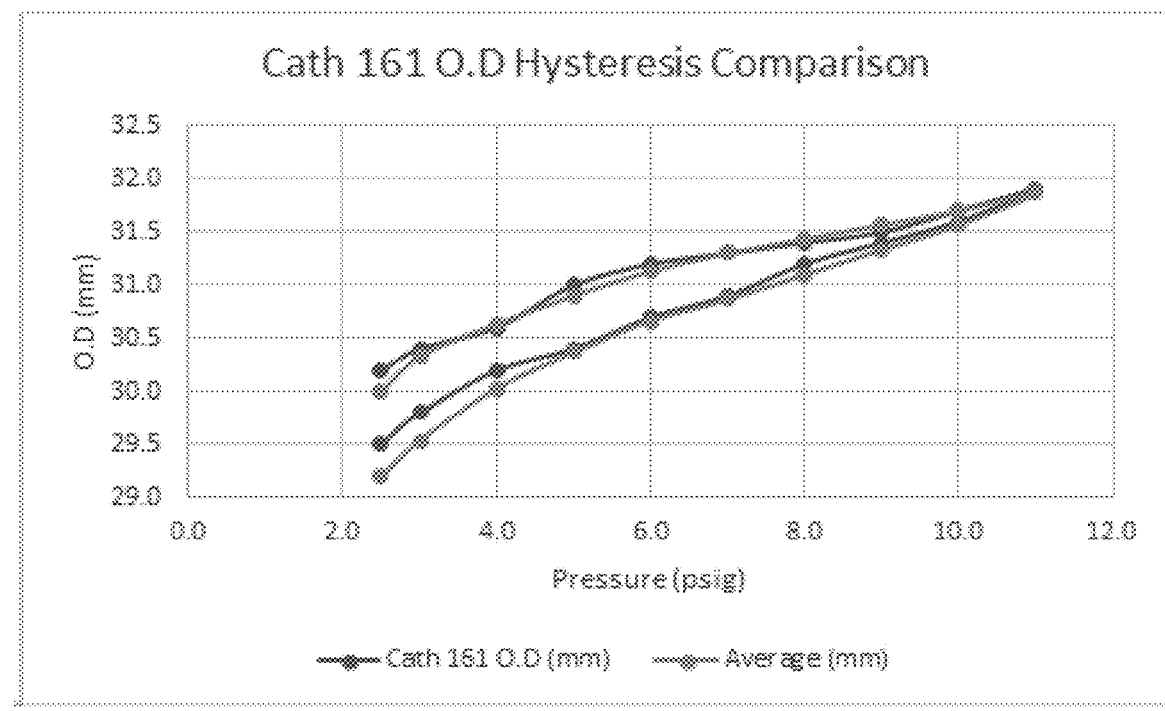
FIG. 5A is a graph of one representative embodiment showing catheter 161 outside diameter hysteresis comparison including outside diameter as a function of pressure.

FIG. 5A is a graph of one representative embodiment showing catheter 161 outside diameter hysteresis comparison including outside diameter (in millimeters) as a function of pressure (in psig).

Figure 5B:
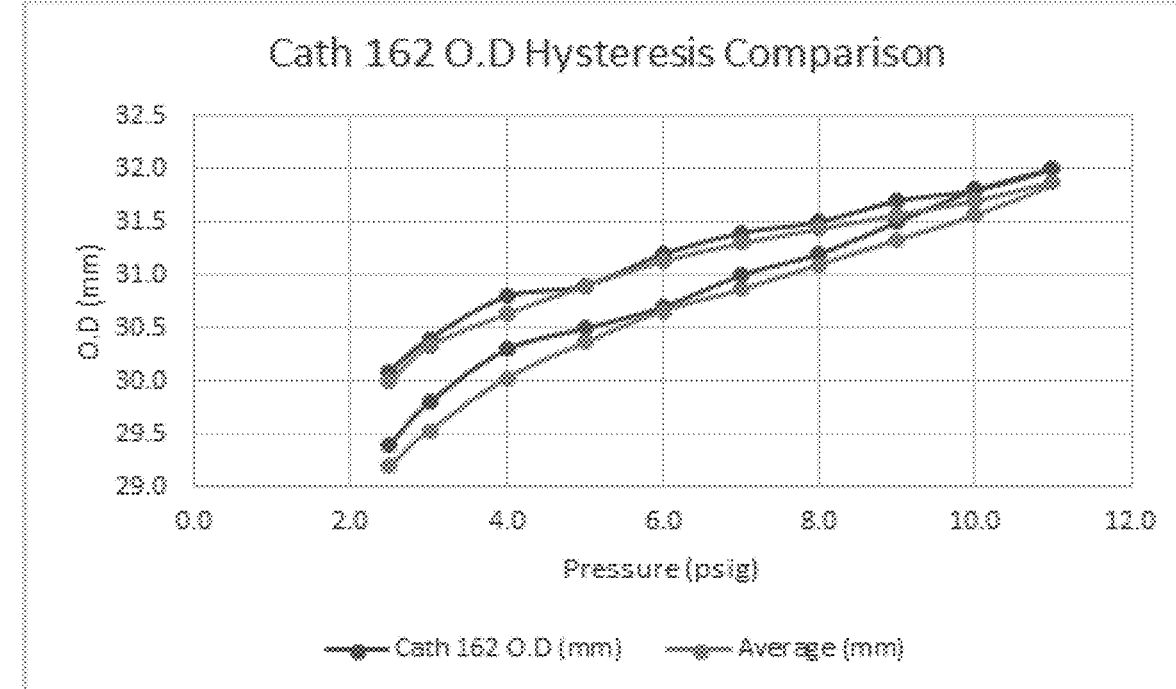
FIG. 5B is a graph of one representative embodiment showing catheter 162 outside diameter hysteresis comparison including outside diameter as a function of pressure.

FIG. 5B is a graph of one representative embodiment showing catheter 162 outside diameter hysteresis comparison including outside diameter (in millimeters) as a function of pressure (in psig).

Figure 5C:
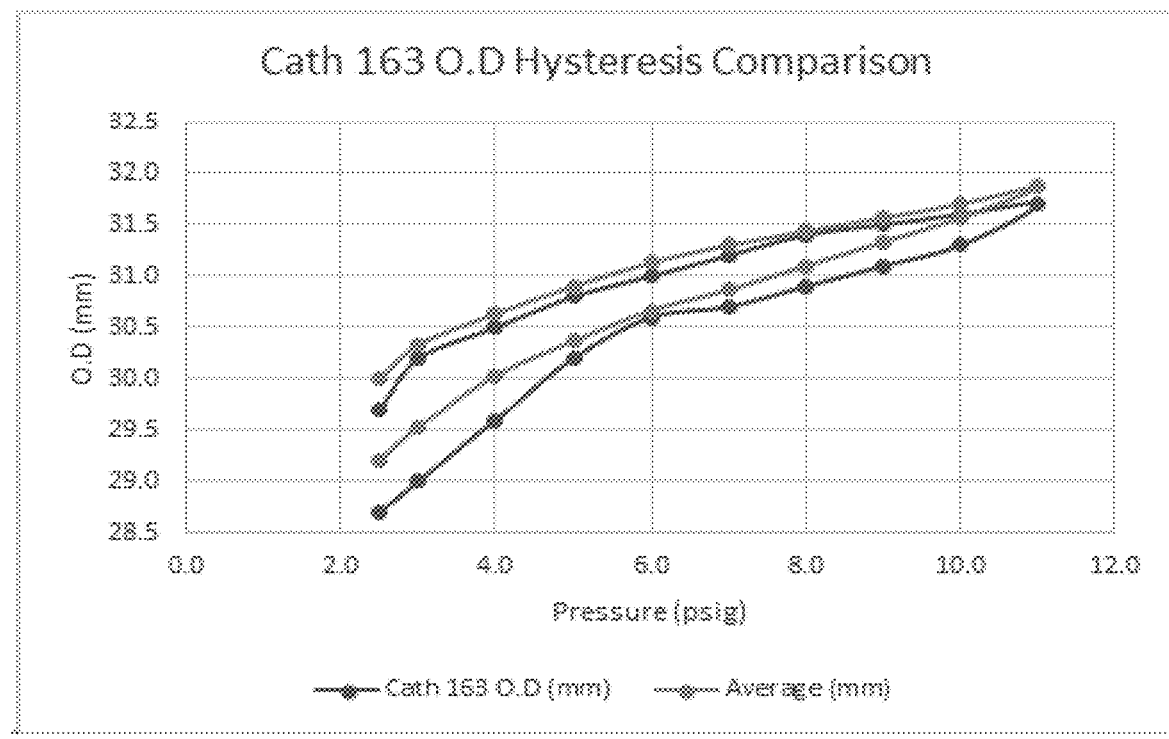
FIG. 5C is a graph of one representative embodiment showing catheter 163 outside diameter hysteresis comparison including outside diameter as a function of pressure.

FIG. 5C is a graph of one representative embodiment showing catheter 163 outside diameter hysteresis comparison including outside diameter (in millimeters) as a function of pressure (in psig).

Figure 5D:
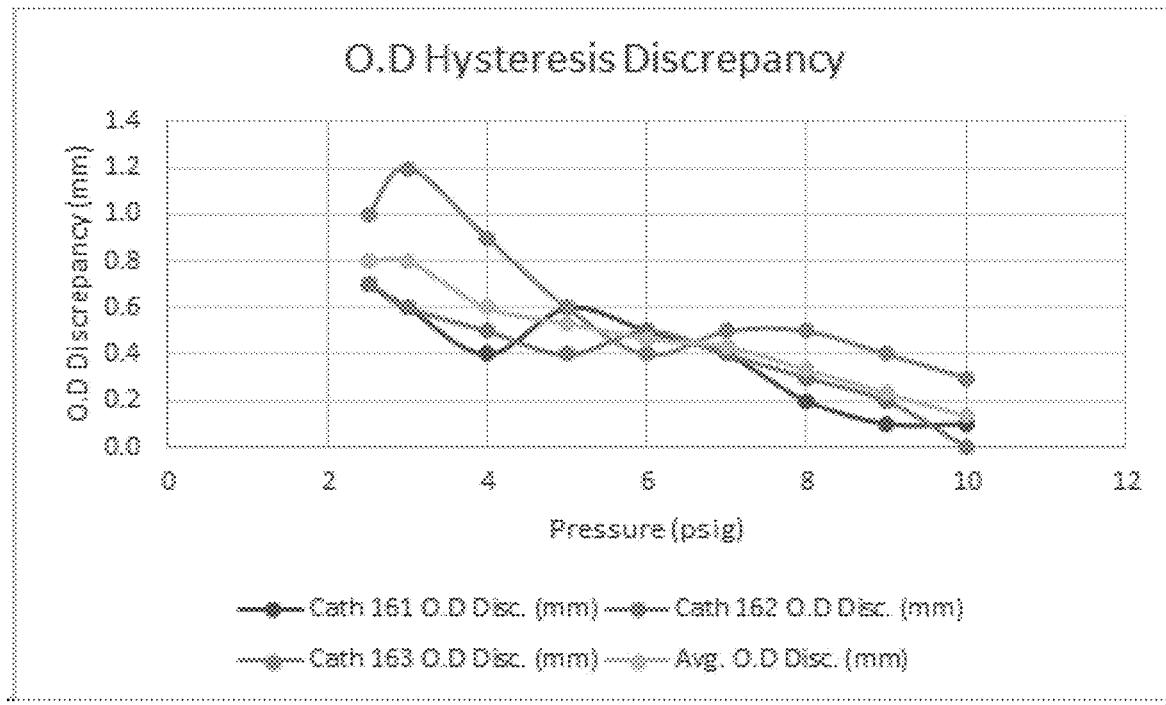
FIG. 5D is a graph of one representative embodiment showing outside diameter hysteresis discrepancy including outside diameter discrepancy as a function of pressure.

FIG. 5D is a graph of one representative embodiment showing outside diameter hysteresis discrepancy including outside diameter discrepancy (in millimeters) as a function of pressure (in psig).

FIG. 5E is a table of one representative embodiment showing hysteresis measurements including outside diameter (in millimeters) as a function of pressure (in psig).

FIG. 5F is a graph of one representative embodiment showing outside diameter discrepancy including outside diameter discrepancy (in millimeters) as a function of pressure (in psig).

In various embodiments, the representative empirical data shown in FIGS. 3A-3B, 4A-4D and 5A-5F can be utilized by the control system, either directly or indirectly, to selectively control the balloon inflation pressure, compensating for balloon hysteresis so as to achieve a desired inflated balloon diameter. In one embodiment, the empirical data can be used to create a look-up table, stored within the control system, which can be queried by the control system for purposes of selecting the inflation pressure corresponding to a specified inflated balloon diameter.

It is understood that although a number of different embodiments of the balloon catheter have been illustrated and described herein, one or more features of any one embodiment can be combined with one or more features of one or more of the other embodiments, provided that such combination satisfies the intent of the present disclosure.

Various modifications and additions can be made to the exemplary embodiments discussed without departing from the scope of the present disclosure. For example, while the embodiments described above refer to particular features, the scope of this disclosure also includes embodiments having different combinations of features and embodiments that do not include all of the described features. Accordingly, the scope of the present disclosure is intended to embrace all such alternatives, modifications, and variations as fall within the scope of the claims, together with all equivalents thereof.

We claim:

1. A balloon catheter system comprising:
    a balloon catheter including a balloon having a balloon interior, the balloon configured to undergo one or more inflation cycles;
    a fluid source that contains a fluid that is selectively delivered to the balloon interior; and
    a control system configured to control the delivery of the fluid to the balloon interior at a first inflation pressure to achieve a first targeted balloon diameter, the first inflation pressure being selected by the control system based on a number of inflation cycles undergone by the balloon;
    wherein the control system is configured to select the first inflation pressure based on empirical data stored within the control system; and
    wherein the empirical data includes data on at least two of balloon materials, balloon dimensions, balloon compliance, inflation pressure, and previous number of balloon inflations of the balloon.

2. The balloon catheter system of claim 1, wherein the empirical data includes data on at least three of data on balloon materials, balloon dimensions, balloon compliance, inflation pressure, and previous number of balloon inflations of the balloon.

3. The balloon catheter system of claim 1, wherein the empirical data includes data on at least four of balloon materials, balloon dimensions, balloon compliance, inflation pressure, and previous number of balloon inflations of the balloon.

4. The balloon catheter system of claim 1, wherein the control system is further configured to control the delivery of the fluid to the balloon interior at a second inflation pressure to achieve a second targeted balloon diameter, the second inflation pressure being selected by the control system based on the number of inflation cycles undergone by the balloon.

5. The balloon catheter system of claim 4, wherein the second inflation pressure is different than the first inflation pressure.

6. The balloon catheter system of claim 5, wherein the second targeted balloon diameter is different than the first targeted balloon diameter.

7. The balloon catheter system of claim 5, wherein the second targeted balloon diameter is the same as the first targeted balloon diameter.

8. The balloon catheter system of claim 4, wherein the control system is further configured to select the second inflation pressure based on empirical data stored within the control system; and wherein the empirical data includes data on at least two of balloon materials, balloon dimensions, balloon compliance, inflation pressure, and previous number of balloon inflations of the balloon.

9. The balloon catheter system of claim 1, wherein control system is configured to select the first inflation pressure so as to achieve the first targeted balloon diameter upon an initial inflation or after one or more previous inflations of the balloon.

10. The balloon catheter system of claim 1, further comprising a handle assembly that is configured to be used by an operator to control the balloon catheter.

11. The balloon catheter system of claim 10, wherein the control system is positioned at least partially within the handle assembly.

12. The balloon catheter system of claim 1, further comprising a control console operatively coupled to the balloon catheter, wherein the control system is at least partially disposed within the control console.

13. The balloon catheter system of claim 1 wherein the balloon is formed from one or more of polyether block amides and polyurethane.

14. A balloon catheter system for use by an operator for treating a targeted vein, the balloon catheter system comprising:
    a balloon catheter including a balloon having a balloon interior, the balloon configured to undergo one or more inflation cycles;
    a fluid source that contains a cryogenic fluid that is selectively delivered to the balloon interior; and
    a control system configured to selectively control the delivery of the fluid to the balloon interior and to selectively adjust an inflation pressure of the balloon interior based on a number of inflation cycles undergone by the balloon so as to selectively adjust an inflated diameter of the balloon;

wherein selectively controlling the delivery of the cryogenic fluid includes selectively controlling an inflation pressure based on empirical data stored within a control system of the cryoablation catheter system, the empirical data including data on at least two of balloon materials, balloon dimensions, balloon compliance, inflation pressure, and previous number of balloon inflations of the balloon.

15. The balloon catheter system of claim 14, wherein the control system is configured to selectively adjust the inflation pressure based on empirical data stored within the control system.

16. The balloon catheter system of claim 15, wherein the empirical data includes at least one of data on balloon materials, balloon dimensions, balloon compliance, inflation pressure, and previous number of balloon inflations of the balloon.

17. The balloon catheter system of claim 16, further comprising a handle assembly that is configured to be used by an operator to control the balloon catheter, wherein the control system is positioned at least partially within the handle assembly.

18. The balloon catheter system of claim 16, further comprising a control console operatively coupled to the balloon catheter, wherein the control system is at least partially disposed within the control console.

19. A method of controlling an inflated diameter of a balloon of a cryoablation catheter balloon of a cryoablation catheter system, the method comprising selectively controlling a delivery of a cryogenic fluid to an interior of the cryoballoon, including selectively controlling an inflation pressure of the balloon based on empirical data stored within a control system of the cryoablation catheter system, the empirical data including data on at least three of balloon materials, balloon dimensions, balloon compliance, inflation pressure, and previous number of balloon inflations of the balloon.

* * * * *